(12) United States Patent
Lee et al.

(10) Patent No.: US 12,292,435 B2
(45) Date of Patent: May 6, 2025

(54) APPARATUS FOR DIAGNOSING LUNG CANCER BASED ON EXHALED BREATH AND METHOD FOR DIAGNOSING SAME

(71) Applicants: ELECTRONICS AND TELECOMMUNICATIONS RESEARCH INSTITUTE, Daejeon (KR); SEOUL NATIONAL UNIVERSITY HOSPITAL, Seoul (KR)

(72) Inventors: Dae-Sik Lee, Daejeon (KR); Sang Hoon Jheon, Seoul (KR); Hyung-Kun Lee, Daejeon (KR); Yoohwa Hwang, Seongnam-si (KR); Doyeob Kim, Daejeon (KR); Chang-Beom Kim, Daejeon (KR); Jin Oh Lee, Daejeon (KR)

(73) Assignees: Electronics and Telecommunications Research Institute, Daejeon (KR); Seoul National University Hospital, Seoul (KR)

( * ) Notice: Subject to any disclaimer, the term of this patent is extended or adjusted under 35 U.S.C. 154(b) by 219 days.

(21) Appl. No.: 17/978,096

(22) Filed: Oct. 31, 2022

(65) Prior Publication Data
US 2023/0296583 A1  Sep. 21, 2023

(30) Foreign Application Priority Data
Mar. 18, 2022 (KR) .................. 10-2022-0033989

(51) Int. Cl.
| | | |
|---|---|---|
| G01N 33/497 | (2006.01) | |
| G01N 1/22 | (2006.01) | |
| G01N 33/00 | (2006.01) | |

(52) U.S. Cl.
CPC ......... G01N 33/497 (2013.01); G01N 1/2205 (2013.01); G01N 33/0047 (2013.01);
(Continued)

(58) Field of Classification Search
CPC ............. G01N 33/497; G01N 33/0047; G01N 33/4975; G01N 33/0016; G01N 1/2205; G01N 2800/12
See application file for complete search history.

(56) References Cited

U.S. PATENT DOCUMENTS

| | | | | |
|---|---|---|---|---|
| 3,317,356 A | * | 5/1967 | Clendinning | ............. C23C 8/80 |
| | | | | 976/DIG. 84 |
| 3,776,635 A | * | 12/1973 | Haskell | ................. G01J 5/0014 |
| | | | | 356/51 |

(Continued)

FOREIGN PATENT DOCUMENTS

| | | | |
|---|---|---|---|
| CN | 211927805 U | * | 11/2020 |
| KR | 20090019717 A | | 2/2009 |

(Continued)

OTHER PUBLICATIONS

Staerz et al. "Understanding the Potential of WO3 Based Sensors for Breath Analysis", Sensors 2016, 16, 1815 <https://www.mdpi.com/1424-8220/16/11/1815> (Year: 2016).*
(Continued)

*Primary Examiner* — Jonathan M Dunlap
(74) *Attorney, Agent, or Firm* — Rabin & Berdo, P.C.

(57) ABSTRACT

Provided are an apparatus for diagnosing a disease and a method for diagnosing same. The apparatus includes a pump for pumping respiratory gas, a first pre-treatment portion connected to the pump and removing moisture and bad breath in the respiratory gas, and a volatile organic compound detector connected between the first pre-treatment
(Continued)

portion and the pump and detecting volatile organic compounds in the respiratory gas.

17 Claims, 7 Drawing Sheets

(52) U.S. Cl.
CPC ..... *G01N 33/0016* (2013.01); *G01N 33/4975* (2024.05); *G01N 2800/12* (2013.01)

(56) References Cited

U.S. PATENT DOCUMENTS

| | | | | |
|---|---|---|---|---|
| 5,620,564 | A * | 4/1997 | Akhtar | D21C 5/005 162/72 |
| 5,733,515 | A * | 3/1998 | Doughty | C01B 32/336 95/137 |
| 5,824,918 | A * | 10/1998 | Zuk | G01N 17/002 73/147 |
| 6,493,638 | B1 * | 12/2002 | McLean | G01N 33/0031 702/22 |
| 9,144,396 | B2 | 9/2015 | Choe | |
| 2006/0257288 | A1 * | 11/2006 | Sun | G01N 27/404 422/89 |
| 2008/0128285 | A1 | 6/2008 | Moon et al. | |
| 2011/0308522 | A1 * | 12/2011 | Kimm | A61M 16/105 55/482.1 |
| 2013/0168548 | A1 * | 7/2013 | Wang | G01N 27/622 250/288 |
| 2014/0165705 | A1 * | 6/2014 | Li | G01N 1/44 73/864.81 |
| 2015/0250407 | A1 * | 9/2015 | Rigas | A61B 5/7275 600/532 |
| 2017/0105656 | A1 * | 4/2017 | Rigas | G01N 33/497 |
| 2017/0191953 | A1 * | 7/2017 | Rigas | G01N 33/84 |
| 2017/0299536 | A1 | 10/2017 | Tsuboi et al. | |
| 2018/0271406 | A1 | 9/2018 | Furusaki et al. | |
| 2019/0187135 | A1 | 6/2019 | Kim et al. | |
| 2020/0088668 | A1 * | 3/2020 | Swager | G01N 27/126 |
| 2020/0179910 | A1 * | 6/2020 | Park | B01J 23/42 |
| 2022/0039690 | A1 * | 2/2022 | Rigas | A61B 5/201 |

FOREIGN PATENT DOCUMENTS

| | | | |
|---|---|---|---|
| KR | 20090061864 | A * | 6/2009 |
| KR | 1020100101876 | A | 9/2010 |
| KR | 101521418 | B1 | 5/2015 |
| KR | 20170082335 | A | 7/2017 |

OTHER PUBLICATIONS

Bajtarevic et al. "Noninvasive detection of lung cancer by analysis of exhaled breath", BMC Cancer 2009, 9, 348 <https://doi.org/10.1186/1471-2407-9-348> (Year: 2009).*

Kim et al. "Gas sensor measurement system capable of sampling volatile organic compounds (VOCs) in wide concentration range", Sensors and Actuators B: Chemical, vol. 122, Iss 1 (2007) 211-218 <https://doi.org/10.1016/j.snb.2006.05.023> (Year: 2007).*

Gang Peng et al., "Diagnosing lung cancer in exhaled breath using gold nanoparticles", Nature Nanotechnology, Aug. 30, 2009, vol. 4, pp. 669-673.

Ji-Eun Chang et al., "Analysis of volatile organic compounds in exhaled breath for lung cancer diagnosis using a sensor system", Sensors and Actuators B 255 (2018) 800-807, Feb. 2018.

Sung H. Lim et al., "An optoelectronic nose for the detection of toxic gases", Nature Chemistry, Oct. 2009, vol. 1, pp. 562-567.

* cited by examiner

APPARATUS FOR DIAGNOSING LUNG CANCER BASED ON EXHALED BREATH AND METHOD FOR DIAGNOSING SAME

CROSS-REFERENCE TO RELATED APPLICATIONS

This U.S. non-provisional patent application claims priority under 35 U.S.C. § 119 of Korean Patent Application No. 10-2022-0033989, Mar. 18, 2022, the entire contents of which are hereby incorporated by reference.

BACKGROUND

The present disclosure herein relates to a disease diagnostic apparatus and a disease diagnostic method therefor, and more particularly, to a disease diagnosis apparatus for lung cancers and a disease diagnostic method therefor.

In general, gas sensors have been applied in a wide range of fields such as environmental monitoring, industrial safety, breathalyzer testing, and food industry, and are expected to be applied to new fields such as medical and space industries in the future. The gas sensors are arranged in the form of array and are being developed as electronic noses or electronic olfactory systems.

SUMMARY

The present disclosure provides a disease diagnostic apparatus capable of enhancing the reliability of detection of volatile organic compounds in respiratory gas.

Disclosed is a disease diagnostic apparatus. An embodiment of the inventive concept provides a disease diagnostic apparatus including: a pump configured to pump respiratory gas; a first pre-treatment portion connected to the pump and configured to remove moisture and bad breath in the respiratory gas; a second pre-treatment portion disposed between the first pre-treatment portion and the pump and configured to regulate humidity of the respiratory gas; a third pre-treatment portion disposed between the second pre-treatment portion and the pump and configured to regulate noise of non-polar volatile organic compounds in the respiratory gas; and a volatile organic compound detector connected between the third pre-treatment portion and the pump and configured to detect volatile organic compounds in the respiratory gas.

In an embodiment, the disease diagnostic apparatus may further include a fourth pre-treatment portion which is connected between the third pre-treatment portion and the volatile organic compound detector and regulates noise of polar volatile organic compounds in the respiratory gas.

In an embodiment, the fourth pre-treatment portion may include: a phenol bubbler configured to evaporate a phenol solution; and a phenol gas sensor disposed between the phenol bubbler and the volatile organic compound detector and configured to detect a phenol gas in the volatile organic compounds.

In an embodiment, the phenol bubbler may include: a phenol bath configured to store the phenol solution; and a first carrier gas supplier which is connected to the phenol bath and provides a first carrier gas into the phenol solution to generate the phenol gas.

In an embodiment, the first pre-treatment portion may include: a first chamber; a moisture filter disposed in the first chamber and configured to remove the moisture; and a bad breath filter disposed between the moisture filter and the volatile organic compound detector and configured to remove the bad breath.

In an embodiment, the first pre-treatment portion further may include a first heater which is disposed inside the first chamber and surrounds the moisture filter and the bad breath filter.

In an embodiment, the second pre-treatment portion may include: a water bubbler configured to evaporate DI water; and a hygrometer provided between the water bubbler and the volatile organic compound detector and configured to detect humidity of the respiratory gas.

In an embodiment, the water bubbler may include: a water bath configured to store the DI water; and a second carrier gas supplier which is connected to the water bath and provides a second carrier gas into the DI water to generate water vapor of the DI water.

In an embodiment, the third pre-treatment portion may include: a benzene bubbler configured to evaporate a benzene solution; and a non-polar volatile organic compound gas sensor disposed between the benzene bubbler and the volatile organic compound detector and configured to detect a benzene gas in the volatile organic compounds.

In an embodiment, the benzene bubbler may include: a benzene bath configured to store the benzene solution; and a third carrier gas supplier which is connected to the benzene bath and provides a third carrier gas into the benzene solution to generate the benzene gas.

In an embodiment of the inventive concept, a disease diagnostic apparatus includes: a first intake line; a volatile organic compound detector connected to the first intake line and configured to detect volatile organic compounds in respiratory gas; a first pre-treatment portion connected between the volatile organic compound detector and the first intake line and configured to remove moisture and bad breath in the respiratory gas; a second pre-treatment portion connected between the first pre-treatment portion and the volatile organic compound detector and configured to regulate humidity of the respiratory gas; a third pre-treatment portion connected between the second pre-treatment portion and the volatile organic compound detector and configured to regulate noise of non-polar volatile organic compounds in the respiratory gas; and a fourth pre-treatment portion connected between the third pre-treatment portion and the volatile organic compound detector and configured to regulate noise of polar volatile organic compounds in the respiratory gas.

In an embodiment, the disease diagnostic apparatus may include: a second intake line configured to connect the fourth pre-treatment portion to the volatile organic compound detector; a third intake line configured to connect the first pre-treatment portion to the second pre-treatment portion; a fourth intake line configured to connect the second pre-treatment portion to the third pre-treatment portion; a fifth intake line configured to connect the third pre-treatment portion to the fourth pre-treatment portion; and a first bypass line which is branched from the first intake line and connected to the second intake line, thereby bypassing the first pre-treatment portion.

In an embodiment, the disease diagnostic apparatus may further include a second bypass line which is branched from the first bypass line and connected to the second intake line, thereby bypassing the second pre-treatment portion.

In an embodiment, the disease diagnostic apparatus may further include a third bypass line which is branched from the second bypass line and connected to the second intake line, thereby bypassing the third pre-treatment portion.

In an embodiment, the disease diagnostic apparatus may further include a fourth bypass line which is branched from the third bypass line and connected to the second intake line, thereby bypassing the fourth pre-treatment portion.

In an embodiment of the inventive concept, a disease diagnostic method includes: pumping respiratory gas; removing moisture in the respiratory gas by using a moisture filter; removing bad breath in the respiratory gas by using a bad breath filter; regulating humidity of the respiratory gas to reference humidity by evaporating DI water; regulating concentration of benzene gas in the respiratory gas to first reference concentration by evaporating a benzene solution; and detecting volatile organic compounds in the respiratory gas by using a sensor array, thereby determining whether a lung cancer is in the human body.

In an embodiment, the disease diagnostic method may further include regulating concentration of phenol gas in the respiratory gas to second reference concentration by evaporating a phenol solution.

In an embodiment, the disease diagnostic method may further include regulating humidity of the respiratory gas to reference humidity by evaporating DI water.

In an embodiment, the reference humidity may be 40% to 60%.

In an embodiment, the first reference concentration may be 0.1 ppm to 0.5 ppm.

BRIEF DESCRIPTION OF THE FIGURES

The accompanying drawings are included to provide a further understanding of the inventive concept, and are incorporated in and constitute a part of this specification. The drawings illustrate embodiments of the inventive concept and, together with the description, serve to explain principles of the inventive concept. In the drawings.

DETAILED DESCRIPTION

Figure 1:
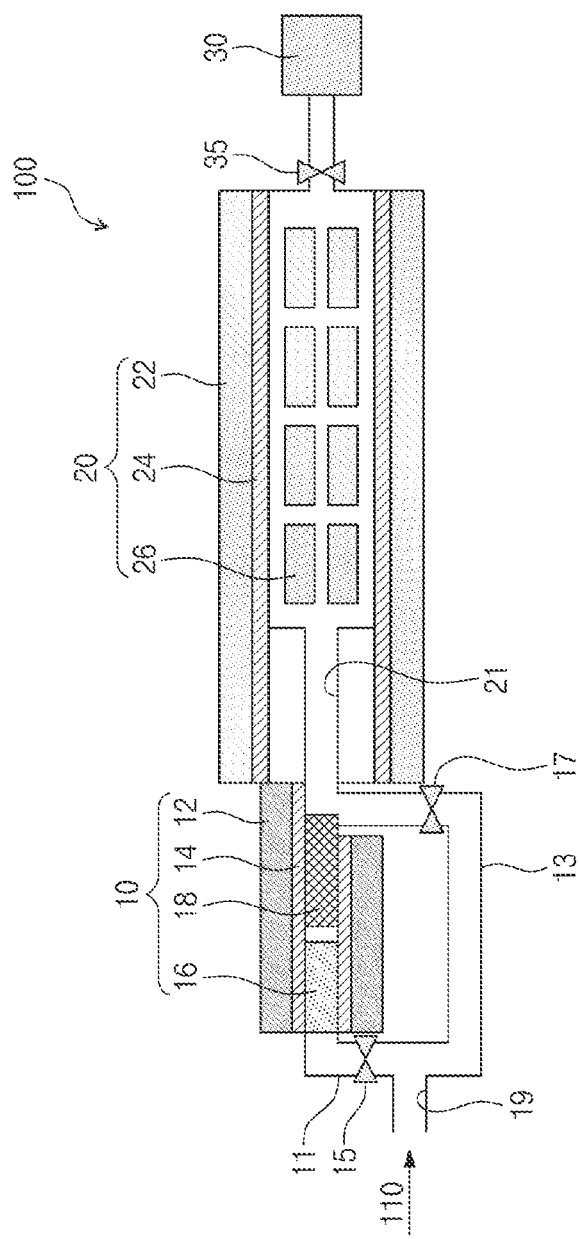
FIG. 1 is a cross-sectional view showing an example of a disease diagnostic apparatus according to an embodiment of the inventive concept.

Hereinafter, embodiments of the inventive concept will be described in detail with reference to the accompanying drawings. Advantages and features of the present disclosure, and implementation methods thereof will be clarified through following embodiments described in detail with reference to the accompanying drawings. The present disclosure may, however, be embodied in different forms and should not be construed as limited to the embodiments set forth herein. Rather, these embodiments are provided so that this disclosure will be thorough and complete, and will fully convey the concept of the present disclosure to those skilled in the art. Further, the present disclosure is only defined by scopes of claims. Like reference numerals refer to like elements throughout.

The terms used herein are used only for explaining embodiments while not limiting the present disclosure. In this specification, the singular forms include the plural forms as well, unless the context clearly indicates otherwise. The meaning of 'comprises' and/or 'comprising' used in the specification does not exclude the presence or addition of one or more components, steps, operations, and/or elements other than the mentioned components, steps, operations, and/or devices. Also, in the specification, respiratory gas, a sensor, and volatile organic compounds may be understood as having meanings mainly used in the field of bio. Since preferred embodiments are provided below, the order of the reference numerals given in the description is not limited thereto.

The foregoing description is about detailed examples for practicing the inventive concept. The present disclosure may include not only the above-described embodiments but also simply changed or easily modified embodiments. In addition, the present disclosure may also include techniques which may be easily modified and practiced by using the above-described embodiments.

FIG. 1 shows an example of a disease diagnostic apparatus 100 according to an embodiment of the inventive concept.

Referring to FIG. 1, the disease diagnostic apparatus 100 according to an embodiment of the inventive concept may include a lung cancer diagnostic apparatus. The disease diagnostic apparatus 100 according to an embodiment of the inventive concept may detect volatile organic compounds (hereinafter, referred to as VOCs) and diagnose the lung cancer. According to an example, the disease diagnostic apparatus 100 according to an embodiment of the inventive concept may include a first pre-treatment portion 10, a volatile organic compound (VOC) detector 20, and a pump 30.

The first pre-treatment portion 10 may be connected between the VOC detector 20 and an inlet 19 of a first intake line 11. The first pre-treatment portion 10 may treat respiratory gas 110, which flows in through the first intake line 11, prior to detection of the VOCs. The respiratory gas 110 may include moisture of the human body (e.g., a subject), bad breath (e.g., $H_2S$, $H_2$, $CH_3SH$), non-polar VOCs (e.g., benzene, hexane), and polar VOCs (e.g., toluene, alcohol, acetone), but the embodiment of the inventive concept is not limited thereto. The first pre-treatment portion 10 may remove the moisture and the bad breath (e.g., $H_2S$, $H_2$, $CH_3SH$) in the respiratory gas 110. According to an example, the first pre-treatment portion 10 may include a first chamber 12, a first heater 14, a moisture filter 16, and a bad breath filter 18.

The first chamber 12 may surround the first heater 14, the moisture filter 16, and the bad breath filter 18, and may protect same. For example, the first chamber 12 may include metal or plastic, but the embodiment of the inventive concept is not limited thereto.

The first heater 14 may be disposed in the first chamber 12. The first heater 14 may surround the moisture filter 16 and the bad breath filter 18. The first heater 14 may heat the respiratory gas 110 in the first intake line 11 to a temperature higher than room temperature. When the VOC detector 20 does not detect the VOCs, the first heater 14 may heat the moisture filter 16 and the bad breath filter 18 to clean and/or initialize same, but the embodiment of the inventive concept is not limited thereto.

The moisture filter 16 may be disposed in the first heater 14 and adjacent to the inlet 19 of the first intake line 11. The moisture filter 16 may absorb moisture in the respiratory gas 110. For example, the moisture filter 16 may include cotton. Also, the moisture filter 16 may include graphite, but the embodiment of the inventive concept is not limited thereto.

The bad breath filter 18 may be disposed, between the moisture filter 16 and the VOC detector 20, in the first heater 14. The bad breath filter 18 may remove the bad breath (e.g., $H_2S$, $H_2$, $CH_3SH$) in the respiratory gas 110. The bad breath filter 18 may include metal powder or metal grains. For example, the bad breath filter 18 may include copper oxide (CuO) or platinum (Pt). Also, the bad breath filter 18 may include metal powder and/or metal grains of selenium oxide ($CeO_2$). On the other hand, the bad breath filter 18 may include a polymer resin (e.g., silicone), a carbon compound, or an organometallic compound, but the embodiment of the inventive concept is not limited thereto.

A first bypass line 13 may be branched from the inlet 19 of the first intake line 11 and connected to a second intake line 21. The first bypass line 13 may bypass the first pre-treatment portion 10. When a first intake valve 15 of the first intake line 11 is closed, the first bypass line 13 may provide the respiratory gas 110 from the inlet 19 of the first intake line 11 to the VOC detector 20 without the removal of the moisture and the bad breath. According to an example, the first bypass line 13 may have a first bypass valve 17. The first bypass valve 17 may be opened and closed in a manner opposite to the first intake valve 15. When the moisture and bad breath in the respiratory gas 110 are removed, the first intake valve 15 may be opened, and the first bypass valve 17 may be closed. The respiratory gas 110 may be sequentially provided into the first pre-treatment portion 10 and the VOC detector 20. When the VOC detector 20 is cleaned and/or initialized, the first bypass valve 17 may be opened, and the first intake valve 15 may be closed.

The VOC detector 20 may be connected between the first pre-treatment portion 10 and the pump 30. The VOC detector 20 may detect non-polar VOCs (e.g., benzene, hexane) and polar VOCs (e.g., toluene, alcohol, acetone) of the respiratory gas 110. The VOC detector 20 may include a second chamber 22, a second heater 24, and a sensor array 26.

The second chamber 22 may surround the second heater 24 and the sensor array 26. The second chamber 22 may include metal or plastic, but the embodiment of the inventive concept is not limited thereto.

The second heater 24 may be disposed in the second chamber 22. The second heater 24 may surround the sensor array 26. The second heater 24 may heat the sensor array 26 and activate a sensing layer 207 (FIG. 2) of the sensor array 26. On the other hand, the second heater 24 may heat the sensor array 26 to clean and initialize the sensor array 26, but the embodiment of the inventive concept is not limited thereto.

The sensor array 26 may be provided inside the second heater 24. The sensor array 26 may detect non-polar VOCs (e.g., benzene, hexane) and polar VOCs (e.g., toluene, alcohol, acetone). A control unit (not shown) may use detection signals of the non-polar VOCs and the polar VOCs of the sensor array 26, and may identify a lung cancer of the human body through the respiratory gas 110.

Figure 2:
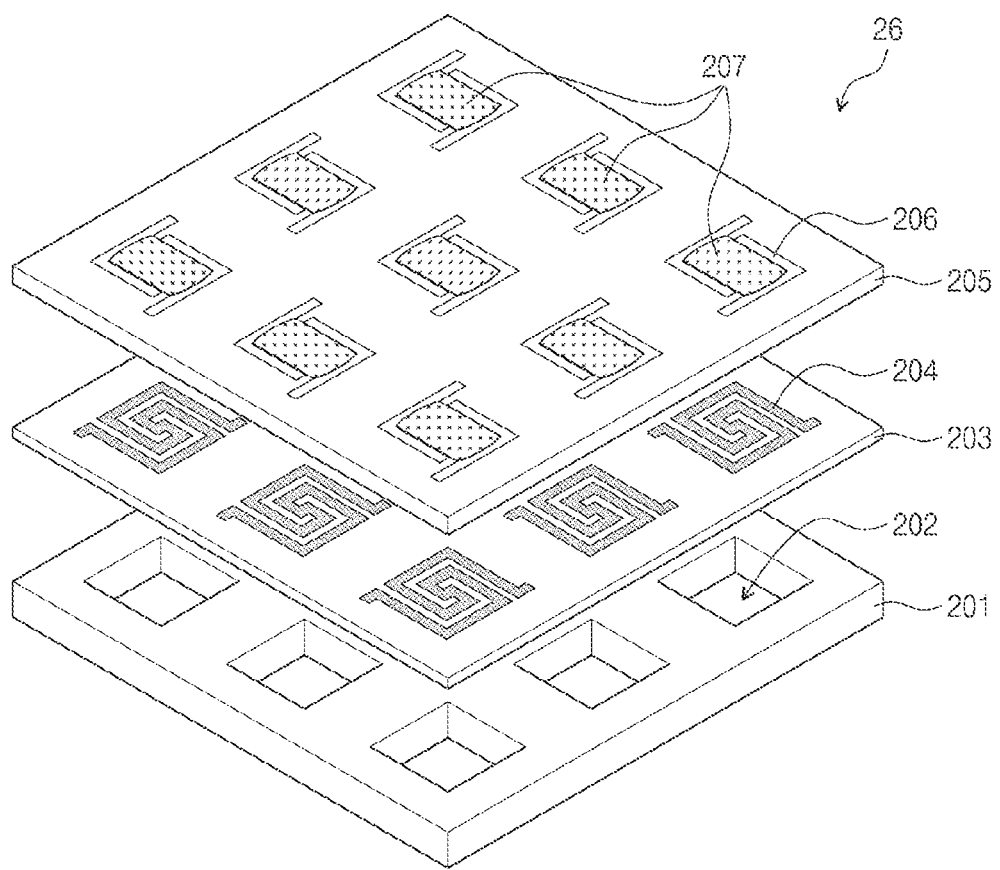
FIG. 2 is a perspective view showing an example of a sensor array of FIG. 1.

FIG. 2 shows an example of the sensor array 26 of FIG. 1.

Referring to FIG. 2, the sensor array 26 may include a substrate 201, a lower insulating film 203, heater electrodes 204, an upper insulating film 205, sensing electrodes 206, and sensing layers 207.

The substrate 201 may include a silicon substrate. According to an example, the substrate 201 may have a plurality of holes 202. The holes 202 may expose a portion of the lower insulating film 203 above the substrate 201. For example, the plurality of holes 202 may be arranged in the form of 3×3 matrices. Furthermore, the plurality of holes 202 may be arranged in the form of N×N matrix. N may be a natural number.

The lower insulating film 203 may be disposed on the substrate 201. The lower insulating film 203 may include silicon oxide or silicon nitride.

The heater electrodes 204 may be disposed on the lower insulating film 203. The heater electrodes 204 may be provided above the holes 202. The heater electrodes 204 may heat the sensing electrodes 206 and the sensing layers 207. For example, the heater electrodes 204 may heat the sensing layers 207 to a temperature ranging from about 200° C. about to 250° C. The heater electrodes 204 may include nickel-chromium alloys.

The upper insulating film 205 may be disposed on the heater electrodes 204 and the lower insulating film 203. The upper insulating film 205 may include silicon oxide or silicon nitride, but the embodiment of the inventive concept is not limited thereto.

The sensing electrodes 206 may be disposed on the upper insulating film 205. The sensing electrodes 206 may be aligned to the heater electrodes 204. The sensing electrodes 206 may include metal, such as gold (Au), silver (Ag), copper (Cu), aluminum (Al), tungsten (W), molybdenum (Mo), indium (In), or cobalt (Co), but the embodiment of the inventive concept is not limited thereto.

A sensing layer 207 may be connected between a pair of sensing electrodes 206. The sensing layers 207 may detect non-polar VOCs (e.g., benzene, hexane) and polar VOCs (e.g., toluene, alcohol, acetone) in the respiratory gas 110. The sensing layers 207 may include metal oxide of $SnO_2$, $WO_3$, $In_2O_3$, ZnO, $Fe_2O_3$, $Zr_2O_3$, and $Co_3O_4$, graphene oxide, or carbon nanotubes, but the embodiment of the inventive concept is not limited thereto. The plurality of the sensing layers 207 may be the same as or different from each other.

Referring back to FIG. 1, the pump 30 may be connected to the first pre-treatment portion 10 and the VOC detector 20. The pump 30 may be connected to the first intake line 11, the first bypass line 13, and the second intake line 21. The pump 30 may pump the respiratory gas 110 in the first intake line 11, the first bypass line 13, the first pre-treatment portion 10, the second intake line 21, and the VOC detector 20. The pump 30 may pump the respiratory gas 110 at pressure lower than atmospheric pressure.

A second intake valve 35 may be connected to the pump 30 and the VOC detector 20. The second intake valve 35 may control the respiratory gas 110 provided into the pump 30. Although not illustrated, the second intake valve 35 may be fastened to the second intake line 21 between the VOC detector 20 and the first pre-treatment portion 10, but the embodiment of the inventive concept is not limited thereto.

Consequently, the disease diagnostic apparatus 100 according to an embodiment of the inventive concept may use the first pre-treatment portion 10 to remove the moisture and bad breath (e.g., $H_2S$, $H_2$, $CH_3SH$) in the respiratory gas 110, thereby improving efficiency of VOCs detection.

Figure 3A:
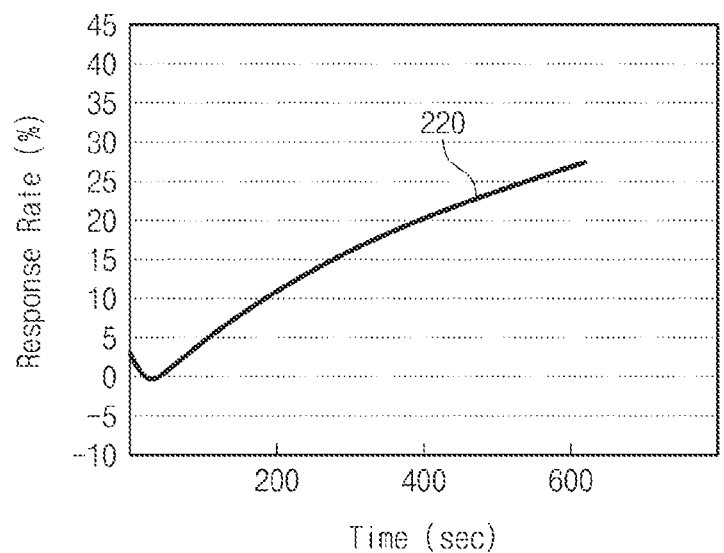
FIGS. 3A and 3B are graphs showing a lung cancer signal or a healthy signal of the respiratory gas of FIG. 1.
Figure 3B:
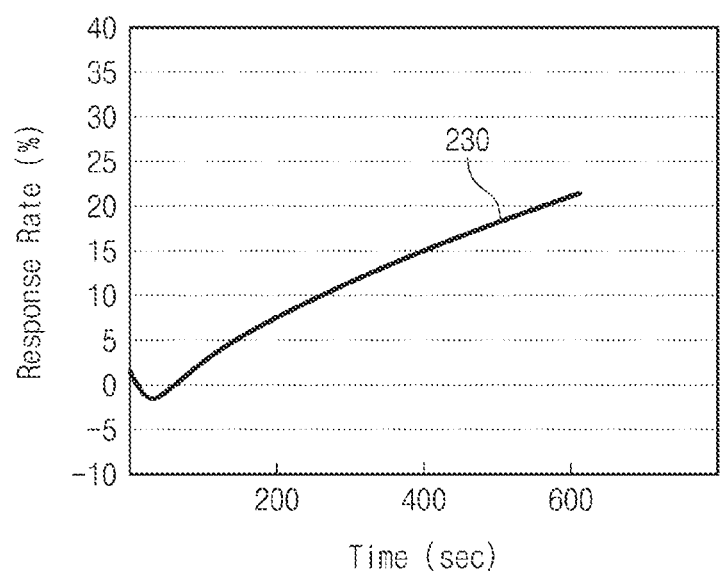

FIGS. 3A and 3B show a lung cancer signal 220 or a healthy signal 230 of the respiratory gas 110 of FIG. 1. In FIGS. 3A and 3B, the horizontal axis represents time, and the vertical axis represents response rates.

Referring to FIGS. 3A and 3B, the lung cancer signal 220 may have a response rate higher than a response rate of the healthy signal 230. The lung cancer signal 220 may have a response rate of about 27% at 600 seconds with respect to the VOCs and relatively large time-varying sensor signal characteristics, and the healthy signal 230 may have a response rate of about 22% at 600 seconds with respect to the VOCs and relatively small time-varying sensor signal characteristics. Therefore, the control unit may compare the response rate of the detection signal of the respiratory gas 110 to the response rates of the lung cancer signal 220 and the healthy signal 230, thereby determining whether the lung cancer is in the human body.

Figure 4:
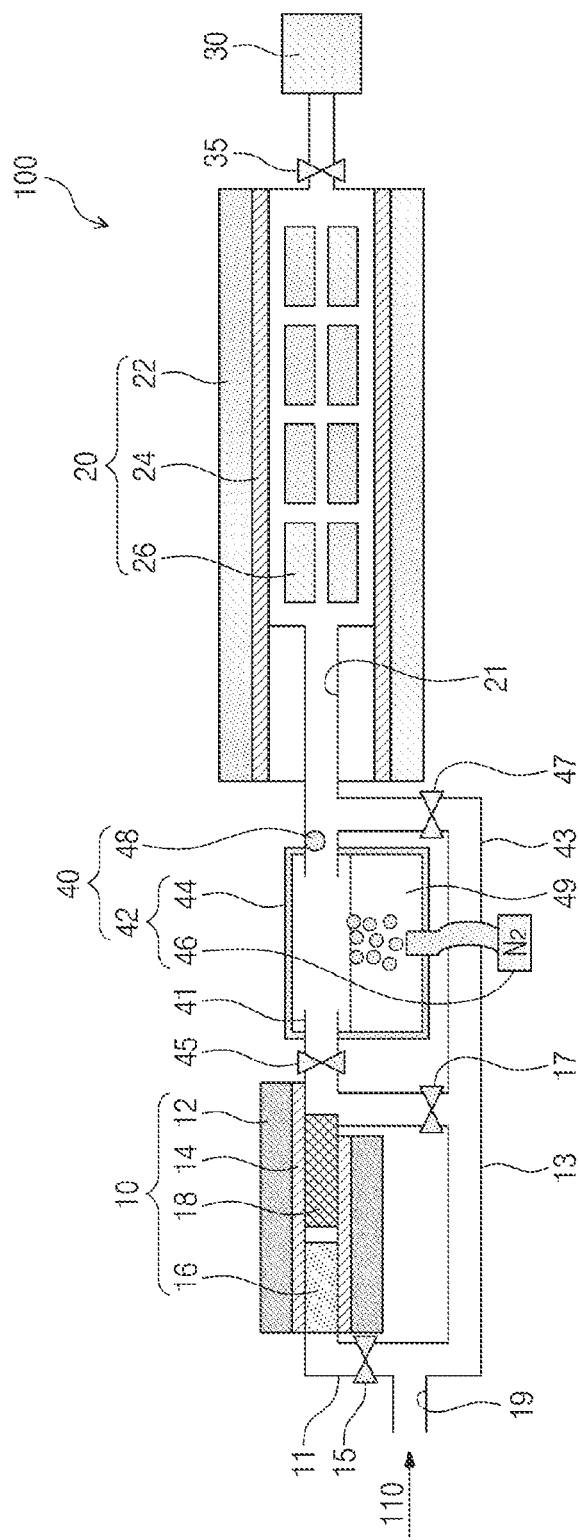
FIG. 4 is a cross-sectional view showing an example of a disease diagnostic apparatus according to an embodiment of the inventive concept.

FIG. 4 shows an example of a disease diagnostic apparatus 100 according to an embodiment of the inventive concept.

Referring to FIG. 4, a disease diagnostic apparatus 100 according to an embodiment of the inventive concept may further include a second pre-treatment portion 40. The second pre-treatment portion 40 may be connected between a first pre-treatment portion 10 and a VOC detector 20. The second pre-treatment portion 40 may regulate humidity of respiratory gas 110. For example, the second pre-treatment portion 40 may regulate the humidity of the respiratory gas 110 to the reference humidity and thus improve the reliability of VOCs detection. The reference humidity may be about 40% to about 60%. When the number of times of VOCs detection of the respiratory gas 110 is increased, the moisture adsorption capabilities of a moisture filter 16 may be deteriorated. When the moisture adsorption capability of the moisture filter 16 is deteriorated, the humidity of the respiratory gas 110 may be gradually increased. When the humidity of the respiratory gas 110 is increased, the efficiency of VOCs detection may be deteriorated. Therefore, the second pre-treatment portion 40 may maintain constant humidity of the respiratory gas 110 irrespective of deterioration in the moisture adsorption capabilities of the moisture filter 16, thereby improving the reliability of VOCs detection. According to an example, the second pre-treatment portion 40 may include a water bubbler 42 and a hygrometer 48.

The water bubbler 42 may be provided between the first pre-treatment portion 10 and the VOC detector 20. The water bubbler 42 may evaporate DI water 49 into the respiratory gas 110 to regulate the humidity of the respiratory gas 110. According to an example, the water bubbler 42 may include a water bath 44 and a first carrier gas supplier 46. The water bath 44 may store the DI water 49. The first carrier gas supplier 46 may provide a first carrier gas (for example, nitrogen, air) into the DI water 49 of the water bath 44, thereby generating water vapor of the DI water 49. When the amount of water vapor is increased, the humidity of the respiratory gas 110 may be increased. When the amount of water vapor is decreased, the humidity of the respiratory gas 110 may be decreased.

The hygrometer 48 may measure the humidity of the respiratory gas 110. A control unit may use a humidity measurement signal of the hygrometer 48 to determine the humidity of the respiratory gas 110. The control unit may regulate the humidity of the respiratory gas 110 in the water bath 44 to the reference humidity and thus improve the reliability of VOCs detection. On the other hand, the water vapor may be provided in an amount of about 1 to 10 ppb by standard gas and mfc.

A third intake line 41 may be connected between the first pre-treatment portion 10 and the second pre-treatment portion 40. The third intake line 41 may deliver the respiratory gas 110 between the first pre-treatment portion 10 and the second pre-treatment portion 40. The third intake line 41 may have a third intake valve 45. The third intake valve 45 may control and/or regulate the respiratory gas 110 in the third intake line 41.

A second bypass line 43 may be branched from a first bypass line 13 and connected to a second intake line 21. The second bypass line 43 may bypass the second pre-treatment portion 40. The second bypass line 43 may provide the respiratory gas 110 to the VOC detector 20 without regulating the humidity. The second bypass line 43 may have a second bypass valve 47. The second bypass valve 47 may be opened and closed in a manner opposite to the third intake valve 45. When the humidity of the respiratory gas 110 is being regulated to the reference humidity, the third intake valve 45 may be opened, and the second bypass valve 47 may be closed. When the humidity of the respiratory gas 110 is not being regulated to the reference humidity, the second bypass valve 47 may be opened, and the third intake valve 45 may be closed.

A first intake line 11, a VOC detector 20, a pump 30, and a second intake valve 35 may have the same configurations as those of FIG. 1.

Figure 5:
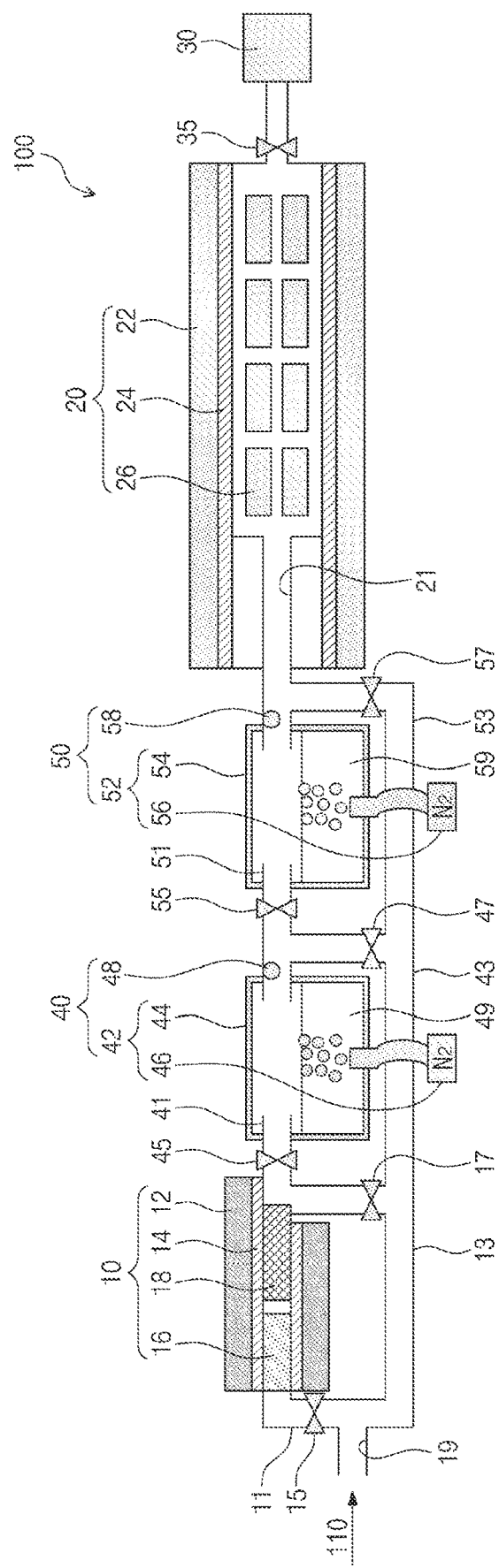
FIG. 5 is a cross-sectional view showing an example of a disease diagnostic apparatus according to an embodiment of the inventive concept.

FIG. 5 shows an example of a disease diagnostic apparatus 100 according to an embodiment of the inventive concept.

Referring to FIG. 5, a disease diagnostic apparatus 100 according to an embodiment of the inventive concept may further include a third pre-treatment portion 50. The third pre-treatment portion 50 may be connected between a second pre-treatment portion 40 and a VOC detector 20. The third pre-treatment portion 50 may regulate concentration of benzene gas (e.g., non-polar VOCs noise) or hexane gas in the VOCs of the respiratory gas 110 to first reference concentration, thereby improving efficiency of VOCs detection. For example, the first reference concentration of the benzene gas may be about 0.01 ppm to about 0.5 ppm. The VOC detector 20 may detect polar VOCs (e.g., toluene, alcohol, acetone) and determine whether a lung cancer exists. A control unit may use a detection signal to acquire the concentrations of the polar VOCs (e.g., toluene, alcohol, acetone), thereby determining whether a lung cancer is in the human body. The existence of lung cancer may be determined in proportion to the concentrations of the polar VOCs (e.g., toluene, alcohol, acetone). According to an example, the third pre-treatment portion 50 may include a benzene bubbler 52 and a non-polar VOC gas sensor 58. In one example for the non-polar VOCs, the benzene bubbler 52 may be connected between the second pre-treatment portion 40 and the VOC detector 20. The benzene bubbler 52 may evaporate a benzene solution 59, thereby regulating the concentrations of non-polar VOCs (e.g., benzene, hexane) in the respiratory gas 110 to the first reference concentration, or removing non-polar substances that interfere with a reaction. When the concentrations of non-polar VOCs are regulated, the efficiency of polar VOCs detection may be improved. According to an example, the benzene bubbler 52 may include a benzene bath 54 and a second carrier gas supplier 56.

The benzene bath 54 may be connected between a third intake line 41 and a second intake line 21. The benzene bath 54 may store the benzene solution 59.

The second carrier gas supplier 56 may provide a second carrier gas (e.g., nitrogen gas) into the benzene solution 59 of the benzene bath 54, thereby generating benzene gas. The benzene gas may be used to regulate the concentration of benzene gas in the respiratory gas 110 to the first reference concentration. On the other hand, the benzene gas may be provided in an amount of about 1 to 10 ppb by standard gas and mfc.

The non-polar VOC gas sensor 58 may be provided in the second intake line 21 and adjacent to the benzene bath 54. The non-polar VOC gas sensor 58 may detect the non-polar VOCs in the respiratory gas 110. The non-polar VOC gas sensor 58 may include a tungsten oxide ($WO_3$) sensor. On the other hand, the VOC detector 20 may include a polar VOC sensor array. For example, a sensing layer 207 of a sensor array 26 may be a polar VOC sensing layer. The sensing layers 207 may include $SnO_2$, $In_2O_3$, ZnO, $Fe_2O_3$, $Zr_2O_3$, $WO_3$, and $Co_3O_4$, but the embodiment of the inventive concept is not limited thereto. The control unit may use detection signals of the non-polar VOCs to detect the concentrations of non-polar VOCs in the respiratory gas 110. The control unit may regulate the concentration of benzene gas in the respiratory gas 110 to the first reference concentration, thereby improving the reliability of polar VOCs detection.

A fourth intake line 51 may be connected between the second pre-treatment portion 40 and the third pre-treatment portion 50. The fourth intake line 51 may deliver the respiratory gas 110 of the second pre-treatment portion 40 to the third pre-treatment portion 50. The fourth intake line 51 may have a fourth intake valve 55. The fourth intake valve 55 may be connected to the fourth intake line 51 adjacent to a second bypass line 43. The fourth intake valve 55 may control the respiratory gas 110 in the fourth intake line 51.

A third bypass line 53 may be connected between the second bypass line 43 and the second intake line 21. The third bypass line 53 is branched from the second bypass line 43 and bypasses the third pre-treatment portion 50 and then may be connected to the second intake line 21. The third bypass line 53 may bypass the third pre-treatment portion 50 and provide the respiratory gas 110 to the VOC detector 20. The third bypass line 53 may have a third bypass valve 57. The third bypass valve 57 may be opened and closed in a manner opposite to the fourth intake valve 55. When the concentration of benzene gas in the respiratory gas 110 is being regulated to the first reference concentration, the fourth intake valve 55 may be opened, and the third bypass valve 57 may be closed. The respiratory gas 110 may be provided into the third pre-treatment portion 50.

When the concentration of benzene gas in the respiratory gas 110 is not being regulated to the first reference concentration, the third bypass valve 57 may be opened, and the fourth intake valve 55 may be closed. The respiratory gas 110 may be provided into the VOC detector 20 after bypassing the third pre-treatment portion 50.

A first pre-treatment portion 10, a first intake line 11, and a first bypass line 13 may have the same configurations as those of FIGS. 1 and 4.

Figure 6:
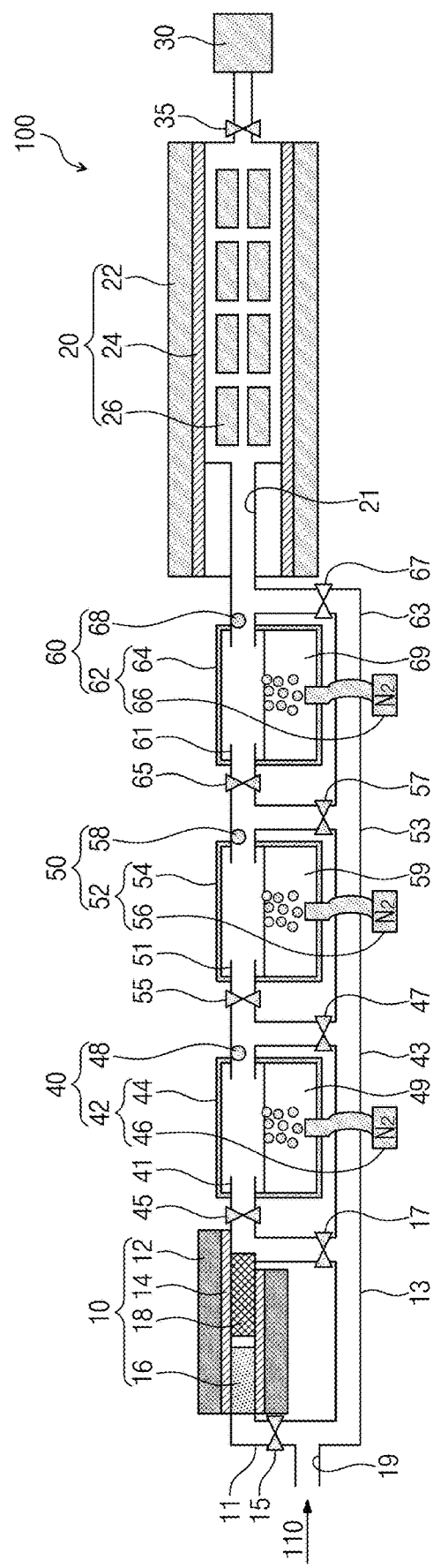
FIG. 6 is a cross-sectional view showing an example of a disease diagnostic apparatus according to an embodiment of the inventive concept.

FIG. 6 shows an example of a disease diagnostic apparatus 100 according to an embodiment of the inventive concept.

Referring to FIG. 6, a disease diagnostic apparatus 100 according to an embodiment of the inventive concept may further include a fourth pre-treatment portion 60. The fourth pre-treatment portion 60 may be connected between the third pre-treatment portion 50 and the VOC detector 20. The fourth pre-treatment portion 60 may regulate concentration of phenol gas (e.g., polar VOCs noise) in the VOCs of the respiratory gas 110 to second reference concentration, thereby improving efficiency of VOCs detection. For example, the second reference concentration of the phenol gas may be about 0.01 ppm to about 0.5 ppm. The VOC detector 20 may detect polar VOCs (e.g., toluene, alcohol, acetone) and determine whether a lung cancer exists. According to an example, the fourth pre-treatment portion 50 may include a phenol bubbler 62 and a phenol gas sensor 68.

The phenol bubbler 62 may be provided between the third pre-treatment portion 50 and the VOC detector 20. The phenol bubbler 62 may evaporate the phenol solution 69 to regulate the concentration of phenol gas in the respiratory gas 110 to the second reference concentration. When the concentrations of polar VOCs noise are regulated, the efficiency of polar VOCs detection may be improved. According to an example, the phenol bubbler 62 may include a phenol bath 64 and a third carrier gas supplier 66.

The phenol bath 64 may be connected between a fourth intake line 51 and a second intake line 21. The phenol bath 64 may store the phenol solution 69.

The third carrier gas supplier 66 may provide a third carrier gas (e.g., nitrogen gas or air) into the phenol solution 69 of the phenol bath 64, thereby generating phenol gas. The phenol gas may be used to regulate the concentration of phenol gas in the respiratory gas 110 to the second reference concentration. On the other hand, the phenol gas may be provided in an amount of about 1 to 10 ppb by standard gas and mfc.

The phenol gas sensor 68 may be provided in the second intake line 21 and adjacent to the phenol bath 64. The phenol gas sensor 68 may detect the phenol gas in the respiratory gas 110. For example, the phenol gas sensor 68 may include a tin oxide ($SnO_2$) sensor. On the other hand, the phenol gas sensor 68 may include zinc oxide (ZnO) or vanadium oxide ($VaO_3$), but the embodiment of the inventive concept is not limited thereto.

A fifth intake line 61 may be connected between the third pre-treatment portion 50 and the fourth pre-treatment portion 60. The fifth intake line 61 may deliver the respiratory gas 110 of the third pre-treatment portion 50 to the fourth pre-treatment portion 60. The fifth intake line 61 may have a fifth intake valve 65. The fifth intake valve 65 may be connected to the fifth intake line 61 adjacent to a third bypass line 53. The fifth intake valve 65 may control the respiratory gas 110 in the fifth intake line 61.

A fourth bypass line 63 may be connected between the third bypass line 53 and the second intake line 21. The fourth bypass line 63 is branched from the third bypass line 53 and bypasses the fourth pre-treatment portion 60 and then may be connected to the second intake line 21. The fourth bypass line 63 may bypass the fourth pre-treatment portion 60 and provide the respiratory gas 110 to the VOC detector 20. The fourth bypass line 63 may have a fourth bypass valve 67. The fourth bypass valve 67 may be opened and closed in a manner opposite to the fifth intake valve 65. When the concentration of phenol gas in the respiratory gas 110 is being regulated to the second reference concentration, the fifth intake valve 65 may be opened, and the fourth bypass valve 67 may be closed. The respiratory gas 110 may be provided into the fourth pre-treatment portion 60.

When the concentration of phenol gas in the respiratory gas 110 is not being regulated to the second reference concentration, the fourth bypass valve 67 may be opened, and the fifth intake valve 65 may be closed. The respiratory gas 110 may be provided into the VOC detector 20 after bypassing the fourth pre-treatment portion 60.

A first pre-treatment portion 10, a first intake line 11, a first bypass line 13, a second pre-treatment portion 40, a third intake line 41, and a second bypass line 43 may have the same configurations as those of FIG. 4.

A disease diagnostic method, which uses the disease diagnostic apparatus 100 having the above configurations according to an embodiment of the inventive concept, will described below.

Figure 7:
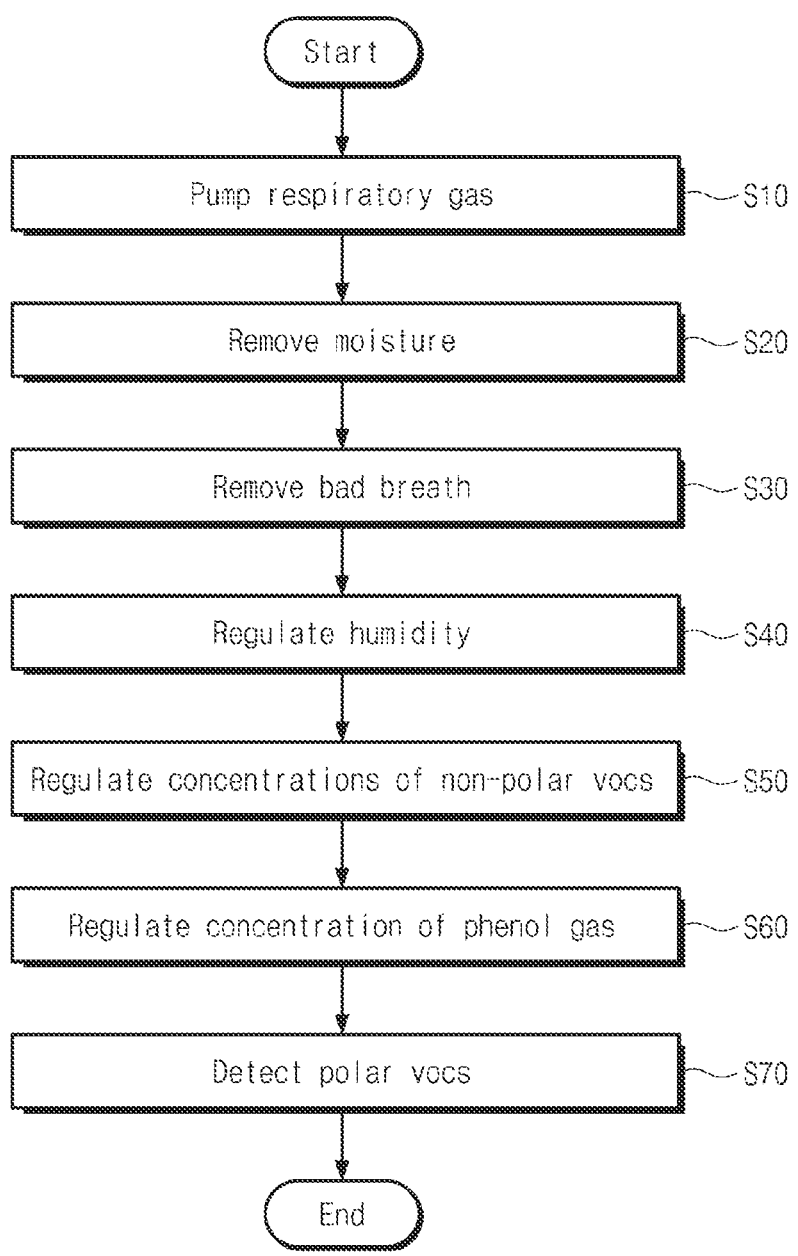
FIG. 7 is a flowchart showing a disease diagnostic method according to an embodiment of the inventive concept.

FIG. 7 shows a disease diagnostic method according to an embodiment of the inventive concept.

Referring to FIG. 7, a pump 30 pumps a respiratory gas 110 through a first intake line 11 and a second intake line 21 (S10). The pump 30 may pump the respiratory gas 110 at low pressure that is lower than atmospheric pressure. A first intake valve 15 and a second intake vale 35 may be opened, and a first bypass valve 17, a second bypass valve 47, a third bypass valve 57, and a fourth bypass valve 67 may be closed. The respiratory gas 110 may be sequentially provided to a moisture filter 16 and a bad breath filter 18 of a first pre-treatment portion 10.

Next, the moisture filter 16 adsorbs moisture in the respiratory gas 110 (S20). The moisture filter 16 may include cotton, but the embodiment of the inventive concept is not limited thereto.

Next, the bad breath filter 18 adsorbs bad breath in the respiratory gas 110 (S30). The bad breath filter 18 may include a polymer resin adsorbent, metal powder and/or metal grains of copper oxide or platinum. The respiratory gas 110 may be provided into a second pre-treatment portion 40 via a third intake line 41. A third intake valve 45 may be opened, and the second bypass valve 47, the third bypass valve 57, and the fourth bypass valve 67 may be closed.

Subsequently, the second pre-treatment portion 40 may regulate humidity of the respiratory gas 110 to reference humidity (S40). The second pre-treatment portion 40 may include a water bubbler 42 and a hygrometer 48. The water bubbler 42 may provide water vapor of DI water 49 into the respiratory gas 110. The hygrometer 48 may detect the humidity of the respiratory gas 110. A control unit may use a humidity detection signal to regulate the humidity of the respiratory gas 110 to the reference humidity, thereby improving the efficiency of VOCs detection. For example, the reference humidity may be about 45% to about 55%. The respiratory gas 110 may be provided into a third pre-treatment portion 50 via a fourth intake line 51. A fourth intake valve 55 may be opened, and the third bypass valve 57 may be closed.

Next, the third pre-treatment portion 50 evaporates a benzene solution 59 to regulate benzene gas in the respiratory gas 110 to first reference concentration (S50). The third pre-treatment portion 50 may include a benzene bubbler 52 and a non-polar VOC gas sensor 58. The benzene bubbler 52 may provide the benzene gas of the benzene solution 59 into the respiratory gas 110. On the other hand, the benzene gas may be provided in an amount of about 1 to 10 ppb by standard gas and mfc. The non-polar VOC gas sensor 58 may detect the non-polar VOCs in the respiratory gas 110. The control unit may use a detection signal of the non-polar VOCs to regulate the concentration of non-polar VOCs in the respiratory gas 110 to the first reference concentration, thereby improving the efficiency of polar VOCs detection. For example, the first reference concentration may be about 0.1 ppm to about 0.5 ppm. The respiratory gas 110 may be provided to a sensor array 26 of the VOC detector 20 via the second intake line 21.

Next, a fourth pre-treatment portion 60 evaporates a phenol solution 69 to regulate phenol gas in the respiratory gas 110 to second reference concentration (S60). The fourth pre-treatment portion 60 may include a phenol bubbler 62 and a phenol gas sensor 68. The phenol bubbler 62 may provide the phenol gas of the phenol solution 69 into the respiratory gas 110. Also, the phenol gas may be provided in an amount of about 1 to 10 ppb by standard gas and mfc. The phenol gas sensor 68 may detect the phenol gas (e.g., polar VOCs noise) in the respiratory gas 110. The control unit may use a detection signal of the phenol gas to regulate the concentration of phenol gas in the respiratory gas 110 to the second reference concentration, thereby improving the efficiency of polar VOCs detection. For example, the second reference concentration of the phenol gas may be about 0.1 ppm to about 0.5 ppm. The respiratory gas 110 may be provided to the sensor array 26 of the VOC detector 20 via the second intake line 21.

Finally, the sensor array 26 detects the polar VOCs (e.g., toluene, alcohol, acetone) in the respiratory gas 110 (S70). The control unit may use a detection signal of the polar VOCs to determine whether a lung cancer is in the human body. The sensor array 26 may include a sensing layer 207 having metal oxide of $SnO_2$, $In_2O_3$, ZnO, $Fe_2O_3$, $Zr_2O_3$, $WO_3$, and $Co_3O_4$.

Activated carbon was widely used in the past to collect VOCs from the atmosphere, but the recovery rate was very low at a low ppb level due to strong adsorption force of the activated carbon. Accordingly, there was a limitation in that samples are lost due to the reaction in the adsorption state. Therefore, polymer resin-based adsorbents have been widely used. Tenax is one of the best known polymer adsorbents. This polymer adsorbent has thermal stability, excellent adsorption/desorption performance and hydrophobic properties, moisture can be excluded during the sample collection. Most polymer-based adsorbents have relatively low retention capacity compared to carbon-based adsorbents. In particular, Tenax is likely to cause erroneous results for some VOCs, such as benzene. Recently, in order to compensate for the limitation of the polymer-based adsorbents, various carbon-based adsorbents that can be used even at high temperatures have been developed. In such a carbon-based adsorbent, the surface of the activated carbon is specially treated, thereby improving adsorption capacity and increasing affinity for organic materials. However, the carbon-based adsorbent is very sensitive to moisture, and when the relative humidity is about 90% or higher, a flow rate of collecting adsorbents may be reduced by 90%. Therefore, there is an urgent need to develop an appropriate pre-treatment module.

As described above, the disease diagnostic apparatus according to the embodiment of the inventive concept may use the first pre-treatment portion, which includes the moisture filter and the bad breath filter, to remove the moisture and bad breath, thereby improving the reliability of detection of the volatile organic compounds in the respiratory gas.

The foregoing description is about detailed examples for practicing the inventive concept. The present disclosure may include not only the above-described embodiments but also simply changed or easily modified embodiments. In addition, the present disclosure may also include techniques which may be easily modified and practiced by using the above-described embodiments.

What is claimed is:

1. A disease diagnostic apparatus comprising:
   a pump configured to pump respiratory gas;
   a first pre-treatment portion connected to the pump and configured to remove moisture and bad breath in the respiratory gas;
   a second pre-treatment portion disposed between the first pre-treatment portion and the pump and configured to regulate humidity of the respiratory gas;
   a third pre-treatment portion disposed between the second pre-treatment portion and the pump and configured to regulate noise of non-polar volatile organic compounds in the respiratory gas;
   a fourth pre-treatment portion which is connected between the third pre-treatment portion and the volatile organic compound detector and regulates noise of polar volatile organic compounds in the respiratory gas; and
   a volatile organic compound detector connected between the third pre-treatment portion and the pump and configured to detect volatile organic compounds in the respiratory gas.

2. The disease diagnostic apparatus of claim 1, wherein the fourth pre-treatment portion comprises:
   a phenol bubbler configured to evaporate a phenol solution; and
   a phenol gas sensor disposed between the phenol bubbler and the volatile organic compound detector and configured to detect a phenol gas in the volatile organic compounds.

3. The disease diagnostic apparatus of claim 2, wherein the phenol bubbler comprises:
   a phenol bath configured to store the phenol solution; and
   a carrier gas supplier which is connected to the phenol bath and provides a carrier gas into the phenol solution to generate the phenol gas.

4. The disease diagnostic apparatus of claim 1, wherein the first pre-treatment portion comprises:
   a first chamber;
   a moisture filter disposed inside the first chamber and configured to remove the moisture; and
   a bad breath filter disposed between the moisture filter and the volatile organic compound detector and configured to remove the bad breath.

5. The disease diagnostic apparatus of claim 4, wherein the first pre-treatment portion further comprises a first heater which is disposed in the first chamber and surrounds the moisture filter and the bad breath filter.

6. The disease diagnostic apparatus of claim 1, wherein the second pre-treatment portion comprises:
   a water bubbler configured to evaporate DI water; and
   a hygrometer provided between the water bubbler and the volatile organic compound detector and configured to detect humidity of the respiratory gas.

7. The disease diagnostic apparatus of claim 6, wherein the water bubbler comprises:
   a water bath configured to store the DI water; and
   a carrier gas supplier which is connected to the water bath and provides a carrier gas into the DI water to generate water vapor of the DI water.

8. The disease diagnostic apparatus of claim 6, wherein the third pre-treatment portion comprises:
   a benzene bubbler configured to evaporate a benzene solution; and
   a non-polar volatile organic compound gas sensor disposed between the benzene bubbler and the volatile organic compound detector and configured to detect a benzene gas in the volatile organic compounds.

9. The disease diagnostic apparatus of claim 8, wherein the benzene bubbler comprises:
   a benzene bath configured to store the benzene solution; and
   a carrier gas supplier which is connected to the benzene bath and provides a carrier gas into the benzene solution to generate the benzene gas.

10. A disease diagnostic apparatus comprising:
    a first intake line;
    a volatile organic compound detector configured to detect volatile organic compounds in respiratory gas;
    a first pre-treatment portion connected between the volatile organic compound detector and the first intake line and configured to remove moisture and bad breath in the respiratory gas;
    a second pre-treatment portion connected between the first pre-treatment portion and the volatile organic compound detector and configured to regulate humidity of the respiratory gas;
    a third pre-treatment portion connected between the second pre-treatment portion and the volatile organic compound detector and configured to regulate noise of non-polar volatile organic compounds in the respiratory gas; and
    a fourth pre-treatment portion connected between the third pre-treatment portion and the volatile organic compound detector and configured to regulate noise of polar volatile organic compounds in the respiratory gas.

11. The disease diagnostic apparatus of claim 10, comprising:
    a second intake line configured to connect the fourth pre-treatment portion to the volatile organic compound detector;
    a third intake line configured to connect the first pre-treatment portion to the second pre-treatment portion;
    a fourth intake line configured to connect the second pre-treatment portion to the third pre-treatment portion;
    a fifth intake line configured to connect the third pre-treatment portion to the fourth pre-treatment portion; and
    a first bypass line which is branched from the first intake line and connected to the second intake line, thereby bypassing the first pre-treatment portion.

12. The disease diagnostic apparatus of claim 11, further comprising a second bypass line which is branched from the first bypass line and the second pre-treatment portion.

13. The disease diagnostic apparatus of claim 12, further comprising a third bypass line which is branched from the second bypass line and the third pre-treatment portion.

14. The disease diagnostic apparatus of claim 13, further comprising a fourth bypass line which bypasses the fourth pre-treatment portion.

15. A disease diagnostic method comprising:
    pumping respiratory gas;
    removing moisture in the respiratory gas by using a moisture filter;
    removing bad breath in the respiratory gas by using a bad breath filter;
    regulating humidity of the respiratory gas to reference humidity by evaporating DI water;
    regulating concentration of benzene gas in the respiratory gas to first reference concentration by evaporating a benzene solution;
    detecting volatile organic compounds in the respiratory gas by using a sensor array, thereby determining whether a lung cancer is in the human body; and regulating concentration of phenol gas in the respiratory gas to second reference concentration by evaporating a phenol solution.

16. The disease diagnostic method of claim 15, wherein the reference humidity is 40% to 60%.

17. The disease diagnostic method of claim 15, wherein the first reference concentration is 0.1 ppm to 0.5 ppm.

* * * * *